United States Patent
Deka et al.

(10) Patent No.: US 8,349,862 B2
(45) Date of Patent: Jan. 8, 2013

(54) PYRIDINE DERIVATIVES FOR THE TREATMENT OF METABOLIC DISORDERS RELATED TO INSULIN RESISTANCE OR HYPERGLYCEMIA

(75) Inventors: Nabajyoti Deka, Mumbai (IN); Sivaramakrishnan Hariharan, Mumbai (IN); Swapnil Ramesh Bajare, Mumbai (IN); Rosalind Adaikalasamy Marita, Mumbai (IN)

(73) Assignee: Piramal Healthcare Limited, Mumbai (IN)

( * ) Notice: Subject to any disclaimer, the term of this patent is extended or adjusted under 35 U.S.C. 154(b) by 0 days.

(21) Appl. No.: 13/222,662

(22) Filed: Aug. 31, 2011

(65) Prior Publication Data

US 2011/0312970 A1    Dec. 22, 2011

Related U.S. Application Data

(62) Division of application No. 12/441,802, filed as application No. PCT/IB2007/053811 on Sep. 20, 2007, now Pat. No. 8,030,324.

(60) Provisional application No. 60/846,194, filed on Sep. 21, 2006, provisional application No. 60/875,672, filed on Dec. 18, 2006.

(51) Int. Cl.
| | |
|---|---|
| *A61K 31/435* | (2006.01) |
| *A61K 31/4439* | (2006.01) |
| *A61P 5/50* | (2006.01) |
| *A61P 3/10* | (2006.01) |
| *A61P 3/04* | (2006.01) |
| *A61P 1/16* | (2006.01) |
| *A61P 7/00* | (2006.01) |
| *A61P 9/12* | (2006.01) |
| *A61P 3/06* | (2006.01) |

(52) U.S. Cl. ........................................ 514/279; 514/339
(58) Field of Classification Search ............. 514/253.12, 514/338
See application file for complete search history.

(56) References Cited

FOREIGN PATENT DOCUMENTS
| WO | WO 01/00579 | 1/2001 |
|---|---|---|
| WO | WO 2006/037501 | 4/2006 |

*Primary Examiner* — Sreeni Padmanabhan
*Assistant Examiner* — Sahar Javanmard
(74) *Attorney, Agent, or Firm* — Frommer Lawrence & Haug LLP

(57) ABSTRACT

The present invention provides novel compounds represented by the general formula (I):

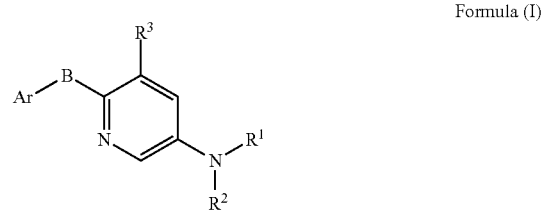

Formula (I)

their stereoisomers, pharmaceutically acceptable salts and their pharmaceutically acceptable solvates thereof, which are useful in treating metabolic disorders related to insulin resistance or hyperglycemia. The invention also relates to a process for the manufacture of compounds of formula (I) and pharmaceutical compositions containing them.

10 Claims, 3 Drawing Sheets

PYRIDINE DERIVATIVES FOR THE TREATMENT OF METABOLIC DISORDERS RELATED TO INSULIN RESISTANCE OR HYPERGLYCEMIA

CROSS-REFERENCE TO RELATED APPLICATION

This application is related to our copending PCT application (PCT/IB2007/053817) entitled: METHOD FOR IDENTIFYING COMPOUNDS THAT ACT AS INSULIN-SENSITIZERS filed on the same date as the present application (20 Sep. 2007).

FIELD OF THE INVENTION

The present invention relates to compounds that are useful in treating metabolic disorders related to insulin resistance or hyperglycemia.

BACKGROUND OF THE INVENTION

Excessive weight, and in extreme cases obesity, is a widespread medical problem. This may be due in part to sedentary life styles and poor diet (high in fats and carbohydrates), as well as to a genetic predisposition in many cases. Obesity is a well-known risk factor for hypertension, Type 2 diabetes and cardiovascular diseases.

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutic control of glucose homeostasis, lipid metabolism and hypertension are critically important in the clinical management and treatment of diabetes mellitus. There are two generally recognized forms of diabetes. In Type 1 diabetes, or insulin-dependent diabetes mellitus (IDDM), patients produce little or no insulin, the hormone that regulates glucose utilization. In Type 2 diabetes, or non-insulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance. Both obesity and Type 2 diabetes are characterized by peripheral tissue insulin resistance.

The prevalence of insulin resistance in glucose intolerant subjects has long been recognized. Reaven et al (American Journal of Medicine, 60, 80, 1976) used a continuous infusion of glucose and insulin (insulin/glucose clamp technique) and oral glucose tolerance tests to demonstrate that insulin resistance existed in a diverse group of nonobese, nonketotic subjects. These subjects ranged from borderline glucose tolerant to overt, fasting hyperglycemia. The diabetic groups in these studies included both insulin dependent (Type 1) and noninsulin dependent (Type 2) subjects.

Coincident with sustained insulin resistance is the more easily determined hyperinsulinemia, which can be measured by accurate determination of circulating plasma insulin concentration in the plasma of subjects. Hyperinsulinemia can be present as a result of insulin resistance, such as is in obese and/or diabetic (Type 2) subjects and/or glucose intolerant subjects, or in Type 1 subjects, as a consequence of overdose of injected insulin compared with normal physiological release of the hormone by the endocrine pancreas.

The independent risk factors such as obesity and hypertension for atherosclerotic diseases are also associated with insulin resistance. Using a combination of insulin/glucose clamps, tracer glucose infusion and indirect calorimetry, it has been demonstrated that the insulin resistance of essential hypertension is located in peripheral tissues (principally muscle) and correlates directly with the severity of hypertension (Diabetes Care, 14, 173, 1991). In hypertension of the obese, insulin resistance generates hyperinsulinemia, which is recruited as a mechanism to limit further weight gain via thermogenesis, but insulin also increases renal sodium reabsorption and stimulates the sympathetic nervous system in kidneys, heart, and vasculature, creating hypertension.

It is now appreciated that insulin resistance is usually the result of a defect in the insulin receptor signaling system, at a site post binding of insulin to the receptor. Accumulated scientific evidence demonstrating insulin resistance in the major tissues which respond to insulin (muscle, liver, adipose), strongly suggests that a defect in insulin signal transduction resides at an early step in this cascade, specifically at the insulin receptor kinase activity, which appears to be diminished (Diabetalogia, 34 (12), 848-861, 1991).

In the recent past, a new class of drugs, which act by reducing peripheral insulin resistance has been developed. These drugs are ligands for the nuclear receptor, peroxisome proliferator-activated receptor gamma isoform (PPAR gamma), expressed primarily in the adipose tissue. These drugs act as insulin sensitizers in reducing blood sugar and hyperinsulinemia. The most common side effects of these PPAR gamma activators are weight gain, edema, increased risk of stroke and heart attack.

Obesity is a disorder characterized by the accumulation of excess fat in the body. Increased incidence of obesity leads to complications such as hypertension, Type 2 diabetes, atherosclerosis, dyslipidemia, osteoarthritis and certain forms of cancer.

Obesity is commonly identified by increased body weight and body mass index (BMI). People with excess body weight are characterized by peripheral tissue insulin resistance. The term 'insulin resistance' refers to decreased biological response to insulin. In obese individual, insulin resistance is often compensated by an increased secretion of insulin from the pancreas. Obese subjects exhibit hyperinsulinemia, an indirect evidence of peripheral insulin resistance. However, the body can increase insulin secretion only to a certain level. Hence if the insulin resistance continues to worsen in an obese person, eventually the body will no longer be able to compensate by stimulating insulin secretion any further. At this time, the plasma insulin levels tend to fall which in turn leads to rise in glucose levels thus precipitating Type 2 diabetes. Clearly, this gradual decline in insulin secretion caused by insulin resistance, initiated by excess fat accumulation, is undesirable for an individual.

Hence, drugs that prevent excess fat accumulation and obesity are desirable. Thus methods and procedures to identify compounds that halt the development of insulin resistance are useful in treating obese individuals. These individuals by virtue of having pharmacological control on insulin resistance will benefit from such treatments in having fewer incidences of heart disease such as elevated blood pressure, abnormal lipid profiles and atherosclerosis.

U.S. Pat. No. 6,583,157 discloses quinolinyl and benzothiazolyl compounds as PPAR modulators.

U.S. Pat. No. 6,403,607 discloses sulfonamide derivatives exhibiting effects in the treatment of peptic ulcer and a drug comprising the derivative as an active ingredient.

U.S. Pat. No. 6,262,112 and U.S. Pat. No. 6,573,278 disclose aryl sulfonamides and analogues and their use in the treatment of neurodegenerative diseases.

There is a need for improved and alternative medicaments for the treatment of metabolic disorders related to insulin resistance or hyperglycemia.

SUMMARY OF THE INVENTION

The present invention provides compounds represented by the general formula (I):

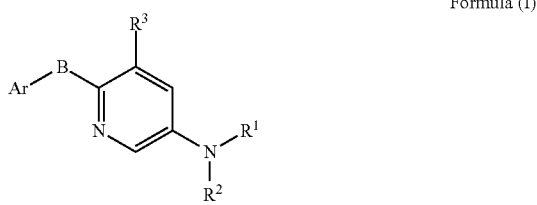

Formula (I)

wherein:
Ar is a phenyl group substituted with heterocyclyl or heteroaryl;
B is —O—, —S—, or —NH—;
$R^1$ is hydrogen;
$R^2$ is $S(O)_2R^4$ or $C(O)(CH_2)_n$—$C(O)OR^5$;
$R^3$ is halogen, cyano, $(CO)OR^6$, or $C(O)NR^7R^8$;
$R^4$ is aryl;
$R^5$ is hydrogen, $(C_1-C_6)$alkyl, or aryl;
$R^6$ is hydrogen or $(C_1-C_4)$alkyl;
$R^7$ and $R^8$ are independently hydrogen or $(C_1-C_6)$alkyl;
n is an integer from 1-3; and
their stereoisomers, pharmaceutically acceptable salts and solvates.

The present invention also relates to a process for the preparation of the compounds of general formula (I) their pharmaceutically acceptable salts, their pharmaceutically acceptable solvates and pharmaceutical compositions containing them.

The present invention relates to compounds of general formula (I) that are useful in treating metabolic disorders related to insulin resistance or hyperglycemia, methods employing such compounds, and use of such compounds.

According to another aspect of the present invention, there are provided methods for manufacture of medicaments including compounds of general formula (I), which are useful for the treatment of metabolic disorders related to insulin resistance or hyperglycemia.

DETAILED DESCRIPTION OF THE INVENTION

Definitions

Figure 1:
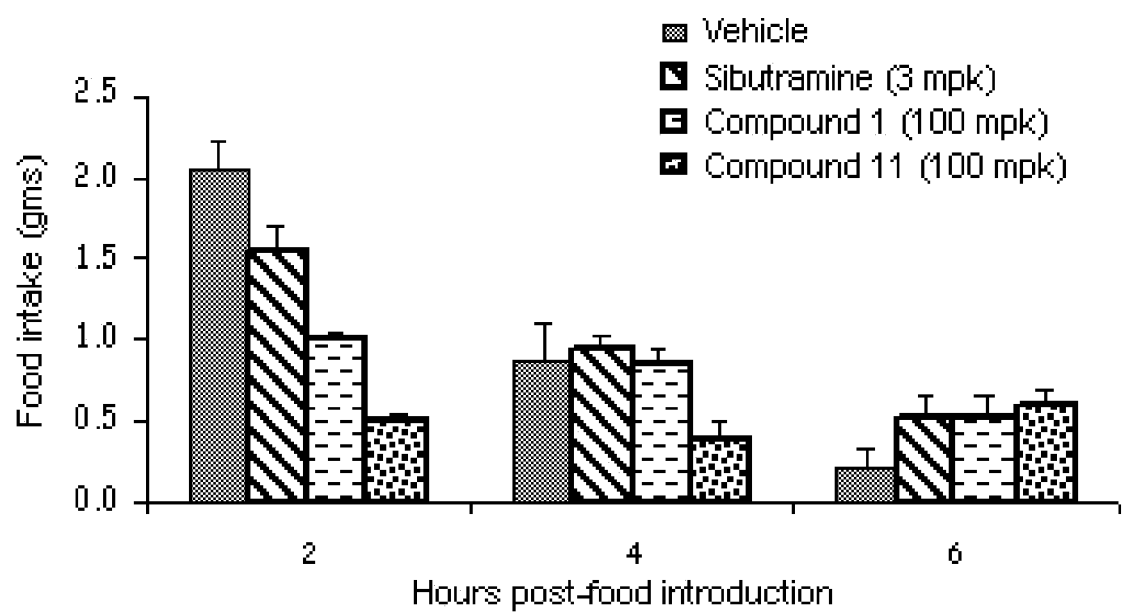
FIG. 1: Effect of compounds on food intake in lean mice.
The effect of standard (Sibutramine), Compound 1 and Compound 11 on food intake in lean C57Bl6/J mice at 2, 4, 6 and 24 hrs post-food introductions is indicated.

Listed below are definitions, which apply to the terms as they are used throughout the specification and the appended claims (unless they are otherwise limited in specific instances), either individually or as part of a larger group.

The term "alkyl," means, unless otherwise stated, a straight or branched chain, or cyclic hydrocarbon radical, or combination thereof, which may be fully saturated, mono- or polyunsaturated, having from one to eight carbon atoms. Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the like.

Unless stated otherwise, alkyl groups can be unsubstituted or substituted by one or more identical or different substituents. Any kind of substituent present in substituted alkyl residues can be present in any desired position provided that the substitution does not lead to an unstable molecule. A substituted alkyl refers to an alkyl residue in which one or more, for example, 1, 2, 3, 4 or 5 hydrogen atoms are replaced with substituents, for example alkyl, halogen, hydroxyl, acyl, carboxyl, alkoxyl, ester, amino, amido, acetamido, fluoroalkyl, aralkyl, acyloxy, aryl, heteroaryl, heterocyclyl, and the like.

As used herein, the term "alkoxyl" or "alkoxy" refers to an alkyl group having an oxygen radical attached thereto, wherein alkyl is as defined above. The terms include, therefore, alkoxyl or alkoxy groups which are substituted by one or more identical or different groups. Representative alkoxy groups include methoxy, trifluoromethoxy, ethoxy, propoxy, tert-butoxy group.

As used herein, the term "acyl" refers to any group or organic radical such as alkyl (which can be further substituted with an alkyl, alkoxy, cycloalkylamino, hydroxy or halo) attached to a carbonyl group, wherein alkyl is as defined above.

The term "heteroatom" refers to nitrogen, oxygen and sulfur. It should be noted that any heteroatom with unsatisfied valences is assumed to have a hydrogen atom to satisfy the valences.

As used herein, the term "aryl" refers to a monocyclic or bicyclic aromatic ring having up to 10 ring carbon atoms. Examples of aryl include phenyl, naphthyl, biphenyl and the like. Unless stated otherwise, aryl residues, for example phenyl or naphthyl, can be unsubstituted or optionally substituted by one or more substituents, for example, up to five identical or different substituents selected from the group consisting of halogen, alkyl, fluoroalkyl, hydroxyl, alkoxy, trifluoromethoxy, cyano, amide, acyl, carboxyl, sulfonyl, aryl, heteroaryl and a heterocyclyl group.

Aryl residues can be bonded via any desired position, and in substituted aryl residues, the substituents can be located in any desired position. For example, in monosubstituted phenyl residues the substituent can be located in the 2-position, the 3-position, the 4-position or the 5-position. If the phenyl group carries two substituents, they can be located in 2,3-position, 2,4-position, 2,5-position, 2,6-position, 3,4-position or 3,5-position.

The term "heteroaryl" means, unless otherwise stated, aryl groups that contain from one to four heteroatoms selected from N, O and S. The ring heteroatoms can be present in any desired number and in any position with respect to each other provided that the resulting heteroaryl system is stable.

Non-limiting examples of heteroaryl groups include pyrrolyl, pyrazolyl, imidazolyl, pyrazinyl, oxazolyl, isoxazolyl, thiazolyl, furyl, thienyl, pyridyl, pyrimidyl, benzothiazolyl, benzimidazolyl, benzooxazolyl, quinolyl, isoquinolyl, quinoxalinyl, and the like.

The terms "heterocyclyl", "heterocyclic" "heterocycle" and "heterocyclo" refer to a saturated, or partially unsaturated monocyclic or bicyclic ring system containing 3, 4, 5, 6, 7, 8, 9, 10 or 11, 12, 13 or 14 ring atoms of which 1, 2, 3 or 4 are identical or different heteroatoms selected from: nitrogen, oxygen and sulfur. The heterocyclyl group may, for example, have 1 or 2 oxygen atoms and/or 1 or 2 sulfur atoms and/or 1 to 4 nitrogen atoms in the ring.

Monocyclic heterocyclyl groups include 3-membered, 4-membered, 5-membered, 6-membered and 7-membered rings. Suitable examples of such heterocyclyl groups are piperidinyl, piperazinyl, tetrahydropyranyl, morpholinyl, thiomorpholinyl, azepanyl and the like.

Bicyclic heterocyclyl groups can include two fused rings, one of which is a 5-, 6- or 7-membered heterocyclic ring and the other of which is a 5-, or 6-membered carbocyclic or heterocyclic ring. Exemplary bicyclic heterocyclic groups include tetrahydroquinolinyl, tetrahydroisoquinolinyl, tetrahydroindolyl and the like.

Unless stated otherwise, the heteroaryl and heterocyclyl groups can be unsubstituted or substituted with one or more (e.g., up to 5), identical or different, substituents. Examples of substituents for the ring carbon and ring nitrogen atoms are: alkyl, alkoxy, halogen, hydroxyl, hydroxyalkyl, fluoroalkyl, aryloxy, amino, cyano, amide, carboxyl, acyl, aryl, heterocyclyl and the like. The substituents can be present at one or more positions provided that a stable molecule results.

The term "arylalkyl" is meant to include those radicals in which an aryl or heteroaryl group is attached to an alkyl group (e.g., benzyl, phenethyl, pyridylmethyl and the like).

The term "halogen" means, unless otherwise stated, a fluorine, chlorine, bromine, or iodine atom.

The term "amino" refers to the group —$NH_2$ which may be optionally substituted with alkyl, acyl, cycloalkyl, aryl, or heterocyclyl wherein the terms alkyl, acyl, cycloalkyl, aryl, or heterocyclyl are as defined herein above.

It will be understood that "substitution" or "substituted with" includes the implicit proviso that such substitution is in accordance with the permitted valence of the substituted atom and the substituent, as well as results in a stable compound, which does not readily undergo transformation such as by rearrangement, cyclization, elimination, etc.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acid and the like. Certain specific compounds of the present invention contain both basic and acidic functionalities that allow the compounds to be converted into either base or acid addition salts.

The neutral form of the compounds may be regenerated by contacting the salt with a base or acid and isolating the parent compound in the conventional manner. The parent form of the compound can differ from the various salt forms in certain physical properties, such as solubility in polar solvents.

Certain compounds of the present invention can exist in unsolvated forms as well as solvated forms, including hydrated forms. In general, the solvated forms and the unsolvated forms are encompassed within the scope of the present invention. Certain compounds of the present invention may exist in multiple crystalline or amorphous forms. In general, all physical forms are within the scope of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Those skilled in the art will recognize that stereocenters exist in compounds of formula (I). Accordingly, the present invention includes all possible stereoisomers and geometric isomers of formula (I) and includes not only racemic compounds but also the optically active isomers as well. When a compound of formula (I) is desired as a single enantiomer, it may be obtained either by resolution of the final product or by stereospecific synthesis from either isomerically pure starting material or any convenient intermediate. Resolution of the final product, an intermediate or a starting material may be effected by conventional techniques. Additionally, in situations wherein tautomers of the compounds of formula (I) are possible, the present invention is intended to include all tautomeric forms of the compounds.

EMBODIMENTS

Embodiments of the Invention

The present invention provides compounds represented by the general formula (I):

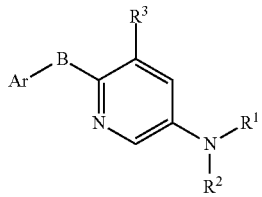

Formula (I)

wherein:
Ar is a phenyl group substituted with heterocyclyl or heteroaryl;
B is —O—, —S—, or —NH—;
$R^1$ is hydrogen;
$R^2$ is $S(O)_2R^4$ or $C(O)(CH_2)_n$—$C(O)OR^5$;
$R^3$ is halogen, cyano, $(CO)OR^6$, or $C(O)NR^7R^8$;
$R^4$ is aryl;
$R^5$ is hydrogen, $(C_1-C_6)$alkyl, or aryl;
$R^6$ is hydrogen or $(C_1-C_4)$alkyl;
$R^7$ and $R^8$ are independently hydrogen or $(C_1-C_6)$alkyl;
n is an integer from 1-3; and
their stereoisomers, pharmaceutically acceptable salts and solvates.

In an embodiment, the present invention provides compounds of formula (I),
wherein:
Ar is a phenyl group substituted with heterocyclyl;
B is —O—, —S—, or NH—;
$R^1$ is hydrogen;
$R^2$ is $S(O)_2R^4$ or $C(O)(CH_2)_n$—$C(O)OR^5$;
$R^3$ is halogen, cyano, $(CO)OR^6$, or $C(O)NR^7R^8$;
$R^4$ is aryl;
$R^5$ is hydrogen, $(C_1-C_6)$alkyl, or aryl;
$R^6$ is hydrogen or $(C_1-C_4)$alkyl;
$R^7$ and $R^8$ are independently hydrogen or $(C_1-C_6)$alkyl;
n is an integer from 1-3; and
their stereoisomers, pharmaceutically acceptable salts and solvates.

In an embodiment, the present invention provides compounds of formula (I),
wherein,
Ar is a phenyl group substituted with heterocyclyl;
B is oxygen;
$R^1$ is hydrogen;
$R^2$ is $S(O)_2R^4$;
$R^3$ is halogen;
$R^4$ is aryl; and
their stereoisomers, pharmaceutically acceptable salts and solvates.

In an embodiment, the present invention provides compounds of formula (I),
wherein,
Ar is a phenyl group substituted with heterocyclyl; such as piperazinyl substituted phenyl with the phenyl moiety coupled to B;
B is oxygen;
$R^1$ is hydrogen;
$R^2$ is $S(O)_2R^4$;
$R^3$ is halogen, preferably chlorine;
$R^4$ is substituted or unsubstituted phenyl; such as phenyl substituted with alkoxy, halogen, cyano, substituted alkyl, or unsubstituted alkyl; such as:
  methyl or substituted-methyl substituted phenyl (e.g., 4-methylphenyl, 2-chloro-4-trifluoromethylphenyl, or 3-chloro-4-methylphenyl);
  mono or di-methoxy substituted phenyl (e.g., 3,4-dimethoxyphenyl, 2,5-dimethoxyphenyl, 4-methoxyphenyl, or 4-trifluoromethoxyphenyl);
  halogen substituted phenyl, such as fluoro substituted phenyl (e.g, 4-fluorophenyl, or 2,4-difluorophenyl), chloro substituted phenyl (e.g., 2,4-dichlorophenyl, 3,4-dichlorophenyl, 2-chloro-4-trifluoromethylphenyl, 3-chloro-4-methylphenyl), or chloro and fluoro substituted phenyl (e.g., 2-fluoro-4-chlorophenyl); or 4-cyanophenyl; and
their stereoisomers, pharmaceutically acceptable salts and solvates.

In an embodiment, the present invention provides compound of formula (I),
wherein,
Ar is 4-(piperazin-1-yl)phenyl with the phenyl moiety coupled to B;
B is oxygen;
$R^1$ is hydrogen;
$R^2$ is $S(O)_2R^4$;
$R^3$ is chlorine;
$R^4$ is 2,4-dichlorophenyl; and
a stereoisomer, pharmaceutically acceptable salt and solvate.

In an embodiment, the present invention provides compounds of formula (I),
wherein,
Ar is 4-(4-acetyl-piperazin-1-yl)phenyl with the phenyl moiety coupled to B;
B is oxygen;
$R^1$ is hydrogen;
$R^2$ is $S(O)_2R^4$;
$R^3$ is chlorine;
$R^4$ is substituted or unsubstituted phenyl; such as phenyl substituted with alkoxy, halogen, cyano, substituted alkyl, or unsubstituted alkyl; such as:
  methyl substituted phenyl (e.g., 4-methylphenyl,);
  mono or di-methoxy substituted phenyl (e.g., 3,4-dimethoxyphenyl, 2,5-dimethoxyphenyl, 4-methoxyphenyl, or 4-trifluoromethoxyphenyl);
  halogen substituted phenyl, such as fluoro substituted phenyl (e.g., 4-fluorophenyl or 2,4-difluorophenyl), chloro substituted phenyl (e.g., 2,4-dichlorophenyl, 3,4-dichlorophenyl, or 2-chloro-4-trifluoromethylphenyl); and
their stereoisomers, pharmaceutically acceptable salts and solvates.

In an embodiment, the present invention provides compounds of formula (I),
wherein,
Ar is 3-(4-methyl-piperazin-1-yl)phenyl with the phenyl moiety coupled to B;
B is oxygen;
$R^1$ is hydrogen;
$R^2$ is $S(O)_2R^4$;
$R^3$ is halogen;
$R^4$ is 4-methoxyphenyl or 2,4-difluorophenyl; and
their stereoisomers, pharmaceutically acceptable salts and solvates.

In an embodiment, the present invention provides compounds of formula (I),
wherein:
Ar is a phenyl group substituted with heteroaryl;
B is —O—, —S—, or NH—;
$R^1$ is hydrogen;
$R^2$ is $S(O)_2R^4$, or $C(O)(CH_2)_n$—$C(O)OR^5$;
$R^3$ is halogen, cyano, $(CO)OR^6$, or $C(O)NR^7R^8$;
$R^4$ is aryl;
$R^5$ is hydrogen, $(C_1$-$C_6)$alkyl, or aryl;
$R^6$ is hydrogen or $(C_1$-$C_4)$alkyl;
$R^7$ and $R^8$ are independently hydrogen or $(C_1$-$C_6)$alkyl;
n is an integer from 1-3; and
their stereoisomers, pharmaceutically acceptable salts and solvates.

In an embodiment, the present invention provides compounds of formula (I),
wherein:
Ar is a phenyl group substituted with heteroaryl;
B is oxygen;
$R^1$ is hydrogen;
$R^2$ is $S(O)_2R^4$;
$R^3$ is halogen, preferably chlorine;
$R^4$ is aryl; and
their stereoisomers, pharmaceutically acceptable salts and solvates.

In an embodiment, the present invention provides compounds of formula (I),
wherein:
Ar is 6-(2-benzo[d]thiazol-2-yl)phenyl with the phenyl moiety coupled to B;
B is oxygen;
$R^1$ is hydrogen;
$R^2$ is $S(O)_2R^4$;
$R^3$ is halogen, preferably chlorine;
$R^4$ is substituted or unsubstituted phenyl; such as phenyl substituted with alkoxy, halogen, cyano, substituted alkyl, or unsubstituted alkyl; such as:
methyl or substituted-methyl substituted phenyl (e.g., 4-methylphenyl);
mono or di-methoxy substituted phenyl (e.g., 3,4-dimethoxyphenyl, 2,5-dimethoxyphenyl, 4-methoxyphenyl, or 4-trifluoromethoxyphenyl);
halogen substituted phenyl, such as fluoro substituted phenyl (e.g., 4-fluorophenyl or 2,4-difluorophenyl) or chloro substituted phenyl (e.g., 2,4-dichlorophenyl, 3,4-dichlorophenyl, or 2-chloro-4-trifluoromethylphenyl); and
their stereoisomers, pharmaceutically acceptable salts and solvates.

In an embodiment, the present invention provides compounds of formula (I),
wherein:
Ar is 6-(2-benzo[d]thiazol-2-yl)phenyl with the phenyl moiety coupled to B;
B is oxygen;
$R^1$ is hydrogen;
$R^2$ is $S(O)_2R^4$;
$R^3$ is chlorine;
$R^4$ is substituted or unsubstituted phenyl; such as phenyl substituted with alkoxy, halogen, cyano, substituted alkyl, or unsubstituted alkyl; such as:
monomethoxy substituted phenyl (e.g., 4-methoxyphenyl); or
chloro substituted phenyl (e.g., 2,4-dichlorophenyl, 3,4-dichlorophenyl, or 2-chloro-4-trifluoromethylphenyl); and their stereoisomers, pharmaceutically acceptable salts and solvates.

In an embodiment, the present invention provides compounds of formula (I),
wherein,
Ar is a phenyl group substituted with heterocyclyl;
B is oxygen;
$R^1$ is hydrogen;
$R^2$ is $C(O)(CH_2)_n$—$C(O)OR^5$;
$R^3$ represents halogen, cyano, $(CO)OR^6$, or $C(O)NR^7R^8$;
$R^5$ is hydrogen, $(C_1$-$C_6)$alkyl, or aryl;
$R^6$ is hydrogen or $(C_1$-$C_4)$alkyl;
$R^7$ and $R^8$ are independently hydrogen or $(C_1$-$C_6)$alkyl;
n is an integer from 1-3; and
their stereoisomers, pharmaceutically acceptable salts and solvates.

In an embodiment, the present invention provides compound of formula (I),
wherein,
Ar is 4-(4-acetyl-piperazin-1-yl)phenyl with the phenyl moiety coupled to B;
B is oxygen;
$R^1$ is hydrogen;
$R^2$ is $C(O)(CH_2)_2$—$C(O)OR^5$;
$R^3$ is chlorine;
$R^5$ is hydrogen; and
a stereoisomer, pharmaceutically acceptable salt and solvate.

Compounds of the present invention are selected from but not limited to:
N-(6-(4-(4-Acetylpiperazin-1-yl)phenoxy)-5-chloropyridin-3-yl)-2,4-dichlorobenzene-sulfonamide,
N-(6-(4-(4-Acetylpiperazin-1-yl)phenoxy)-5-chloropyridin-3-yl)-4-methoxybenzene-sulfonamide,
N-(6-(4-(4-Acetylpiperazin-1-yl)phenoxy)-5-chloropyridin-3-yl)-3,4-dimethoxy-benzene sulfonamide,
N-(6-(4-(4-Acetylpiperazin-1-yl)phenoxy)-5-chloropyridin-3-yl)-2,5-dimethoxy-benzene sulfonamide,
N-(6-(4-(4-Acetylpiperazin-1-yl)phenoxy)-5-chloropyridin-3-yl)-2-chloro-4-(trifluoromethyl)benzenesulfonamide,
N-(6-(4-(4-Acetylpiperazin-1-yl)phenoxy)-5-chloropyridin-3-yl)-3,4-dichlorobenzene-sulfonamide,
N-(6-(4-(4-Acetylpiperazin-1-yl)phenoxy)-5-chloropyridin-3-yl)-4-(trifluoromethoxy)benzene sulfonamide,
N-(6-(4-(4-Acetylpiperazin-1-yl)phenoxy)-5-chloropyridin-3-yl)-4-methylbenzene-sulfonamide,
N-(6-(4-(4-Acetylpiperazin-1-yl)phenoxy)-5-chloropyridin-3-yl)-2,4-difluorobenzene-sulfonamide,
N-(6-(4-(4-Acetylpiperazin-1-yl)phenoxy)-5-chloropyridin-3-yl)-4-fluorobenzene-sulfonamide,
2,4-Dichloro-N-(5-chloro-6-(4-(piperazin-1-yl)phenoxy)pyridin-3-yl)benzenesulfonamide,
N-(5-Chloro-6-(3-(4-methylpiperazin-1-yl)phenoxy)pyridin-3-yl)-2,4-difluorobenzene sulfonamide,
N-(5-Chloro-6-(3-(4-methylpiperazin-1-yl)phenoxy)pyridin-3-yl)-4-methoxybenzene-sulfonamide,
4-(6-(4-(4-Acetylpiperazin-1-yl)phenoxy)-5-chloropyridin-3-ylamino)-4-oxobutanoic acid,
N-(6-(2-(Benzo[d]thiazol-2-yl)phenoxy)-5-chloropyridin-3-yl)-2,4-dichlorobenzene-sulfonamide,
N-(6-(2-(Benzo[d]thiazol-2-yl)phenoxy)-5-chloropyridin-3-yl)-4-methoxybenzene-sulfonamide,
N-(6-(2-(Benzo[d]thiazol-2-yl)phenoxy)-5-chloropyridin-3-yl)-3,4-dichloro-benzenesulfonamide,
N-(6-(2-(Benzo[d]thiazol-2-yl)phenoxy)-5-chloropyridin-3-yl)-2-chloro-4-(trifluoromethyl)benzenesulfonamide; and
their pharmaceutically acceptable salts and solvates.

Suitable compounds of the present invention are selected from but not limited to:

N-(6-(4-(4-Acetylpiperazin-1-yl)phenoxy)-5-chloropyridin-3-yl)-2,4-dichlorobenzene-sulfonamide, 2,4-Dichloro-N-(5-chloro-6-(4-(piperazin-1-yl)phenoxy)pyridin-3-yl)benzenesulfonamide, 4-(6-(4-(4-Acetylpiperazin-1-yl)phenoxy)-5-chloropyridin-3-ylamino)-4-oxobutanoic acid; and their pharmaceutically acceptable salts and solvates.

As used herein, the terms "treat" and "therapy" and the like refer to alleviate, slow the progression, prophylaxis, attenuation or cure of existing disease (e.g., type 2 diabetes, obesity or dyslipidemia).

The term "therapeutically effective amount" as used herein is meant to describe an amount of a compound of the present invention effective in producing the desired therapeutic response in a particular patient suffering from metabolic disorders related to insulin resistance or hyperglycemia.

According to another aspect of present invention there are provided methods for manufacture of medicaments including compounds of general formula (I), which are useful for the treatment of metabolic disorders related to insulin resistance or hyperglycemia.

According to another aspect of present invention there are provided methods for the manufacture of a medicament including compounds of general formula (I), which are useful for the treatment of metabolic disorders related to insulin resistance or hyperglycemia in a mammal, which medicament is manufactured to be administered, either sequentially or simultaneously, with at least one other pharmaceutically active compound.

While it is possible that compounds of the present invention may be therapeutically administered as the raw chemical, it is preferable to present the active ingredient as a pharmaceutical formulation. Accordingly, the present invention further provides for a pharmaceutical formulation including a compound of formula (I) or a pharmaceutically acceptable salt or solvate or a prodrug thereof, for example, together with one or more pharmaceutically acceptable carriers thereof and, optionally, other therapeutic and/or prophylactic ingredients.

The pharmaceutical composition may be in the forms normally employed, such as tablets, lozenges, capsules, powders, syrups, solutions, suspensions and the like specially formulated for oral, buccal, parenteral, transdermal, inhalation, intranasal, transmucosal, implant, or rectal administration, however oral administration is preferred. For buccal administration, the formulation may take the form of tablets or lozenges formulated in conventional manner. Tablets and capsules for oral administration may contain conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycolate) or wetting agents, such as sodium lauryl sulfate. The tablets may be coated according to methods well known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides. Additionally, formulations of the present invention may be formulated for parenteral administration by injection or continuous infusion. Formulations for injection may take such forms as suspensions, solutions, or emulsions in oily or aqueous vehicles, and may contain formulatory agents such as suspending, stabilising and/or dispersing agents. Alternatively, the active ingredient may be in powder form for constitution with a suitable vehicle (e.g., sterile, pyrogen-free water) before use.

The formulations according to the invention may also be formulated as a depot preparation. Such long acting formulations may be administered by implantation (for example, subcutaneously or intramuscularly) or by intramuscular injection. Accordingly, the compounds of the invention may be formulated with suitable polymeric or hydrophobic materials (as an emulsion in an acceptable oil, for example), ion exchange resins or as sparingly soluble derivatives as a sparingly soluble salt, for example.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02-5000 mg per day or 1-1500 mg per day. The desired dose may conveniently be presented in a single dose or as divided doses administered at appropriate intervals, for example as two, three, four or more sub-doses per day.

The formulations according to the invention may contain between 0.1-99% of the active ingredient, conveniently from 30-95% for tablets and capsules and 3-50% for liquid preparations.

Furthermore, in addition to at least one compound of the general formula (I), as active ingredient, the pharmaceutical compositions may also contain one or more other therapeutically active ingredients.

According to an embodiment of the present invention there is provided a method for the treatment of metabolic disorders related to insulin resistance or hyperglycemia, including administering to a mammal in need thereof a therapeutically effective amount of a compound of formula (I).

According to an embodiment of the present invention there is provided a method for the treatment of metabolic disorders related to insulin resistance or hyperglycemia, including type 2 diabetes, obesity, glucose intolerance, dyslipidemia, hyperinsulinemia, atherosclerotic disease, polycystic ovary syndrome, coronary artery disease, hypertension, aging, non alcoholic fatty liver disease, infections, cancer and stroke, including administering to a mammal in need thereof a therapeutically effective amount of a compound of formula (I).

According to an embodiment of the present invention there is provided a method for the treatment of type 2 diabetes and disorders related thereto, including administering to a mammal in need thereof a therapeutically effective amount of a compound of formula (I).

According to an embodiment of the present invention there is provided a method for the treatment of obesity and disorders related thereto, including administering to a mammal in need thereof a therapeutically effective amount of a compound of formula (I).

According to an embodiment of the present invention there is provided a method for the treatment of dyslipidemia and disorders related thereto, including administering to a mammal in need thereof a therapeutically effective amount of a compound of formula (I).

According to an embodiment the compounds of present invention are useful for the treatment of metabolic disorders related to insulin resistance or hyperglycemia.

According to an embodiment the compounds of the present invention are useful for the treatment of metabolic disorders related to insulin resistance or hyperglycemia, including type 2 diabetes, glucose intolerance, dyslipidemia, hyperinsulinemia, atherosclerotic disease, polycystic ovary syndrome, coronary artery disease, hypertension, aging, non alcoholic fatty liver disease, infections, cancer and stroke.

According to an embodiment the compounds of the present invention are useful for the treatment of type 2 diabetes.

According to an embodiment the compounds of the present invention are useful for the treatment of obesity and related disorders.

According to an embodiment the compounds of the present invention are useful for the treatment of dyslipidemia.

Representative compounds useful in the treatment of metabolic disorders related to insulin resistance or hyperglycemia, in accordance with the present invention are selected from but are not limited to the following:

N-(6-(4-(4-Acetylpiperazin-1-yl)phenoxy)-5-chloropyridin-3-yl)-2,4-dichlorobenzene-sulfonamide,
N-(6-(4-(4-Acetylpiperazin-1-yl)phenoxy)-5-chloropyridin-3-yl)-4-methoxybenzene-sulfonamide,
N-(6-(4-(4-Acetylpiperazin-1-yl)phenoxy)-5-chloropyridin-3-yl)-3,4-dimethoxy-benzene sulfonamide,
N-(6-(4-(4-Acetylpiperazin-1-yl)phenoxy)-5-chloropyridin-3-yl)-2,5-dimethoxy-benzene sulfonamide,
N-(6-(4-(4-Acetylpiperazin-1-yl)phenoxy)-5-chloropyridin-3-yl)-2-chloro-4-(trifluoromethyl)benzenesulfonamide,
N-(6-(4-(4-Acetylpiperazin-1-yl)phenoxy)-5-chloropyridin-3-yl)-3,4-dichlorobenzene-sulfonamide,
N-(6-(4-(4-Acetylpiperazin-1-yl)phenoxy)-5-chloropyridin-3-yl)-4-(trifluoromethoxy)benzene sulfonamide,
N-(6-(4-(4-Acetylpiperazin-1-yl)phenoxy)-5-chloropyridin-3-yl)-4-methylbenzene-sulfonamide,
N-(6-(4-(4-Acetylpiperazin-1-yl)phenoxy)-5-chloropyridin-3-yl)-2,4-difluorobenzene-sulfonamide,
N-(6-(4-(4-Acetylpiperazin-1-yl)phenoxy)-5-chloropyridin-3-yl)-4-fluorobenzene-sulfonamide,
2,4-Dichloro-N-(5-chloro-6-(4-(piperazin-1-yl)phenoxy)pyridin-3-yl)benzenesulfonamide,
N-(5-Chloro-6-(3-(4-methylpiperazin-1-yl)phenoxy)pyridin-3-yl)-2,4-difluorobenzene sulfonamide,
N-(5-Chloro-6-(3-(4-methylpiperazin-1-yl)phenoxy)pyridin-3-yl)-4-methoxybenzene-sulfonamide,
4-(6-(4-(4-Acetylpiperazin-1-yl)phenoxy)-5-chloropyridin-3-ylamino)-4-oxobutanoic acid,
N-(6-(2-(Benzo[d]thiazol-2-yl)phenoxy)-5-chloropyridin-3-yl)-2,4-dichlorobenzene-sulfonamide,
N-(6-(2-(Benzo[d]thiazol-2-yl)phenoxy)-5-chloropyridin-3-yl)-4-methoxybenzene-sulfonamide,
N-(6-(2-(Benzo[d]thiazol-2-yl)phenoxy)-5-chloropyridin-3-yl)-3,4-dichloro-benzene sulfonamide,
N-(6-(2-(Benzo[d]thiazol-2-yl)phenoxy)-5-chloropyridin-3-yl)-2-chloro-4-(trifluoromethyl)benzenesulfonamide; and
their pharmaceutically acceptable salts and solvates.

Suitable compounds useful in the treatment of metabolic disorders related to insulin resistance or hyperglycemia, in accordance with the present invention are selected from but are not limited to the following:

N-(6-(4-(4-Acetylpiperazin-1-yl)phenoxy)-5-chloropyridin-3-yl)-2,4-dichlorobenzene-sulfonamide,
2,4-Dichloro-N-(5-chloro-6-(4-(piperazin-1-yl)phenoxy)pyridin-3-yl)benzenesulfonamide,
4-(6-(4-(4-Acetylpiperazin-1-yl)phenoxy)-5-chloropyridin-3-ylamino)-4-oxobutanoic acid; and their pharmaceutically acceptable salts and solvates.

Preparation of the Compounds

According to a further aspect of the invention, there is provided a process for the preparation of compounds of general formula (I),

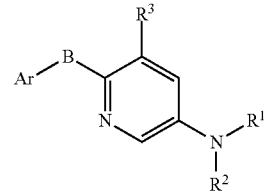

Formula (I)

wherein:

Ar is a phenyl group substituted with heterocyclyl or heteroaryl;

B is —O—, —S—, or —NH—;

$R^1$ is hydrogen;

$R^2$ is $S(O)_2R^4$ or $C(O)(CH_2)_n$—$C(O)OR^5$;

$R^3$ is halogen, cyano, $(CO)OR^6$, or $C(O)NR^7R^8$;

$R^4$ is aryl;

$R^5$ is hydrogen, $(C_1-C_6)$alkyl, or aryl;

$R^6$ is hydrogen or $(C_1-C_4)$alkyl;

$R^7$ and $R^8$ are independently hydrogen or $(C_1-C_6)$alkyl;

n is an integer from 1-3; and their stereoisomers, pharmaceutically acceptable salts and solvates.

The compounds of general formula (I), according to the invention can be prepared by, or in analogy with, standard synthetic methods, and especially according to, or in analogy with, Scheme 1.

Scheme 1

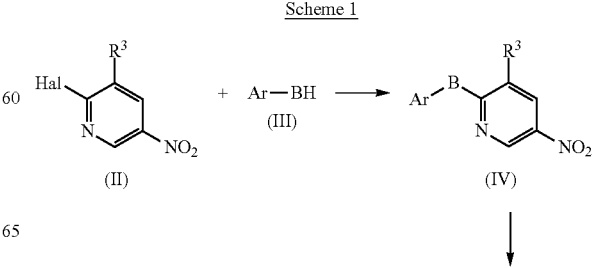

-continued

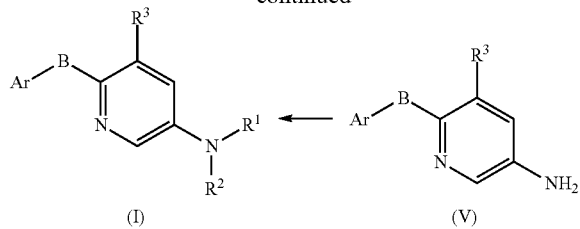

As shown in scheme 1, compounds of the present invention can be prepared by reacting compound of formula (II) wherein $R^3$ is as defined above and Hal is selected from fluorine, chlorine, bromine or iodine with a compound of formula (III) wherein Ar and B are as defined above, in the presence of a solvent such as dimethyl formamide, dimethyl sulfoxide, tetrahydrofuran, dioxane, or acetonitrile, optionally in the presence of a base such as cesium carbonate, potassium carbonate, sodium carbonate, sodium hydroxide, potassium hydroxide, or potassium fluoride to provide the compound of formula (IV) wherein Ar, B and $R^3$ are as defined above. The nitro group of compound of formula (IV) is reduced to the corresponding amino group to obtain compound of formula (V) wherein Ar, B and $R^3$ are as defined above. Reduction of the nitro group may be carried out by using $SnCl_2$ in a solvent such as ethyl acetate; or by using Fe/HCl; or in presence of gaseous hydrogen and a catalyst such as Pd—C, Rh—C, Pt—C; or any suitable method known in the art.

The compound of formula (V) is further converted to the desired compound of formula (I) wherein $R^2$ is —$SO_2R^4$ and Ar, B, $R^1$, $R^3$ and $R^4$ are as defined above, by reacting with Hal-$SO_2R^4$ wherein Hal is represented by fluorine, chlorine, bromine or iodine and $R^4$ is as defined above, in the presence of pyridine or triethyl amine as a base and a solvent selected from acetonitrile, dichloromethane, chloroform, carbon tetrachloride, tetrahydrofuran, or dioxane.

The compound of formula (V) may also be converted to the desired compound of formula (I) wherein $R^2$ is —C(O)(CH$_2$)$_n$—C(O)OH and Ar, B, n, $R^1$, and $R^3$ are as defined above, by refluxing with an anhydride [(CH$_2$)$_n$(CO)$_2$O], in the presence a solvent selected from benzene, toluene, tetrahydrofuran, or dioxane. The acid of formula (I) may be converted to the ester wherein $R^2$ is —C(O)(CH$_2$)$_n$—C(O)OR$^5$ wherein Ar, B, n, $R^1$, and $R^3$ are as defined above and $R^5$ is (C$_1$-C$_4$)alkyl or aryl, by standard esterification reactions known in the literature.

The compounds of general formula I, wherein Ar, B, $R^1$, $R^2$ and $R^3$ are as defined above may be converted into a pharmaceutically acceptable salt by standard procedures known in the literature.

The compounds of this invention can be prepared as illustrated by the accompanying working examples. The following examples are set forth to illustrate the synthesis of some particular compounds of the present invention and to exemplify general processes. Accordingly, the following Examples section is in no way intended to limit the scope of the invention contemplated herein.

EXAMPLES

List of Abbreviations

HCl: Hydrochloric acid;
POCl$_3$: Phosphorous oxychloride;
Cs$_2$CO$_3$: Cesium carbonate
DCM: Dichloromethane
DMF: Dimethylformamide
DMSO: Dimethyl sulfoxide
CPM: Counts per minute
mpk: mg per Kg.
od: Once a day
bid: Twice a day
HEPES: N-(2-hydroxyethyl)-piperazine-N'-2-ethanesulfonic acid
MP (DSC): melting point (Differential Scanning calorimetry)
CMC: Carboxy methyl cellulose Preparation 1: 2,3-Dichloro-5-nitro pyridine Step i. 2-Hydroxy-3-chloro-5-nitro pyridine 2-Hydroxy-5-nitro pyridine (1 g, 7.14 mmol) was added portion wise to 4.5 mL of concentrated HCl under constant stirring and then heated to 50° C. To this was slowly added a solution of sodium chlorate (266 mg, 2.5 mmol) in water (4 mL). The reaction was maintained at the same temperature for an additional hour, and then cooled to 0° C. The precipitate obtained was filtered, washed thoroughly with water and dried to obtain 2-hydroxy-3-chloro-5-nitro pyridine.
Yield: 850 mg, (68.2%); $^1$H NMR (DMSO-d$_6$) δ: 8.36 (d, 1H); 8.65 (d, 1H).

Step ii. 2,3-Dichloro-5-nitro pyridine

Quinoline (0.3 mL, 2.34 mmol) was added to POCl$_3$ (0.5 mL 4.68 mmol) at 0° C. under nitrogen. To this stirred mixture was added 2-hydroxy-3-chloro-5-nitro pyridine (816 mg, 4.68 mmol) obtained in step i above. The reaction mixture was heated at 120° C. for 2 hours, cooled to 0° C. followed by addition of ice-cold water. The precipitate obtained was filtered, washed thoroughly with water and dried to obtain 2,3-dichloro-5-nitro pyridine.
Yield: 630 mg, (70.3%); $^1$H NMR (DMSO-d$_6$) δ: 8.94 (d, 1H); 9.16 (d, 1H).

Preparation 2: 1-{4-[4-((5-Amino-3-chloro-pyridin-2yloxy)-phenyl]-piperazin-1-yl-ethanone Step i. Preparation of 1-{4-[4-((3-Chloro-5-nitro-pyridin-2yloxy)-phenyl]-piperazin-1-yl-ethanone Dry dimethylformamide (10 mL) was added to 1-[4-(-hydroxy-phenyl-piperazine-1-yl]-ethanone (696 mg, 3.16 mmol) with stirring and cesium carbonate was added (1.03 g, 3.16 mmol) at room temperature (25° C.). After 30 minutes 2,3-dichloro-5-nitro-pyridine (610 mg, 3.16 mmol) (as obtained in preparation 1), was added and the stirring was continued further for 18 hours. The solvent was removed under vacuum and to the resulting mass was added water (20 mL), extracted with ethyl acetate, dried over sodium sulfate and concentrated under vacuum to obtain crude product that was further purified by column chromatography (silica gel— ~200 mesh, 30% ethyl acetate in pet ether) to obtain the title compound.
Yield: 1.09 g (92.9%);
$^1$H NMR (CDCl$_3$) δ: 2.01 (s, 3H), 2.99 (t, 2H), 3.05 (t, 2H), 3.54 (s, 4H), 5.30 (s, 2H), 6.85 (d, 1H), 6.93 (d, 1H), 7.17 (s, 1H), 7.43 (s, 1H).

Step ii. 1-{4-[4-((5-Amino-3-chloro-pyridin-2yloxy)-phenyl]-piperazin-1-yl-ethanone Compound of step i (3.15 g, 8.34 mmol) was dissolved in ethyl acetate (50 mL). Stannous chloride dihydrate (7.52 g, 33.36 mmol) was added at room temperature (25° C.) and stirring was continued for 18 hours. Solvent was removed under vacuum and chloroform (50 mL) was added. 1 N sodium hydroxide solution was added until a clear solution was obtained. Separated the organic layer was separated and extracted with chloroform. The chloroform layer was washed with brine & water successively, dried over sodium sulfate and concentrated under vacuum to obtain crude product that was further purified by column chromatography (silica gel—~200 mesh, 1% methanol in chloroform) to obtain the title compound.

Yield: 1.77 g (61.52%); $^1$H NMR (CDCl$_3$) δ: 2.04 (s, 3H), 3.10 (m, 2H), 3.18 (m, 2H), 3.59 (brs, 4H), 5.32 (s, 2H), 7.05 (d, J=9 Hz, 2H), 7.14 (d, J=9 Hz, 2H), 8.86 (d, J=2.4 Hz, 1H), 8.95 (d, J=2.4 Hz, 1H); MS: 347 (M+1).

Preparation 3: 5-Chloro-6-(3-(4-methylpiperazin-1-yl)phenoxy)pyridin-3-amine 3-(4-Methylpiperazin-1-yl)phenol was reacted with 2,3-dichloro-5-nitro pyridine (as obtained in preparation 1), to obtain 1-(3-(3-chloro-5-nitropyridin-2-yloxy)phenyl)-4-methylpiperazine which was further converted to the title compound as per the procedure described in preparation 2.

$^1$H NMR (CDCl$_3$) δ: 3.09 (t, J=4.5 Hz, 4H), 3.22 (t, J=4.5 Hz, 4H), 3.70 (s, 3H), 5.17 (s, 2H), 6.36 (dd, J=2.5, 8.0 Hz, 1H), 6.46 (s, 1H), 6.55 (dd, J=1.5, 8.0 Hz, 1H), 7.06 (d, J=2.5 Hz, 1H), 7.11 (t, J=8.0 Hz, 1H), 7.63 (d, J=2.5 Hz, 1H); MS (ES): 319.01 (M+1).

Preparation 4: 6-(2-(Benzo[d]thiazol-2-yl)phenoxy)-5-chloropyridin-3-amine 2-(Benzo[d]thiazol-2-yl)phenol was reacted with 2,3-dichloro-5-nitro pyridine to obtain 2-(2-(3-chloro-5-nitropyridin-2-yloxy)phenyl)benzo[d]thiazole which was further converted to 6-(2-(benzo[d]thiazol-2-yl)phenoxy)-5-chloropyridin-3-amine as per the procedure described in preparation 2.

$^1$H NMR (DMSO-d$_6$) δ: 5.48 (s, 2H), 6.99 (d, J=8.0 Hz, 1H), 7.27 (d, J=2.5 Hz, 1H), 7.35 (t, J=7.5 Hz, 1H), 7.44 (t, J=7.5 Hz, 1H), 7.47 (d, J=2.5 Hz, 1H), 7.54 (m, 2H), 8.07 (d, J=8.0 Hz, 1H), 8.11 (d, J=8.0 Hz, 1H), 8.46 (d, J=7.0 Hz, 1H); MS: 354.11 (M+1).

General Procedure for Preparation of Compounds of Formula (I)

To a stirred solution of amine [obtained by preparations 1-4] (1 mmol) in DCM, pyridine (1-3 mmol) was added which was followed by addition of substituted benzenesulfonylchloride (1 mmol). The reaction mixture was stirred at room temperature (25° C.). Reaction mixture was diluted using DCM, washed with water, dried over anhydrous sodium sulfate and concentrated. The crude product was purified using column chromatography (silica gel) to obtain the desired compound.

The compounds of examples 1-10, 12, 13, and 15-18 were prepared by this procedure.

General Procedure for Salt Formation

Procedure A: Compound of formula (I) was dissolved in 1:1 ethyl acetate and DCM solvent mixture. To the clear solution 1 equivalent of corresponding acid (such as toluene sulfonic acid or methane sulfonic acid, or benzene sulfonic acid) was added and stirred for 30-45 mins at room temperature (25° C.). The precipitate was filtered off and characterized by $^1$H NMR and MP (DSC).

Procedure B: The said compound of formula (I) was dissolved in ethanol (a large excess was required to obtained a clear solution on heating). To the clear solution, 1 equivalent of the corresponding acid (such as toluene sulfonic acid, methane sulfonic acid, benzene sulfonic acid) was added. After refluxing for 3 hours, the solvent was removed and the solid obtained was characterized by $^1$H NMR and MP (DSC).

Example 1

N-(6-(4-(4-Acetylpiperazin-1-yl)phenoxy)-5-chloropyridin-3-yl)-2,4-dichlorobenzene-sulfonamide
(Compound 1)

The title compound was obtained by reacting 1-(4-(4-(5-amino-3-chloropyridin-2-yloxy)phenyl)piperazin-1-yl)ethanone (obtained as per procedure described in preparation 2) and 2,4-dichlorobenzene-1-sulfonyl chloride.

mp: 215° C.-216° C.; $^1$H NMR (DMSO-d$_6$) δ: 2.02 (s, 3H), 3.02 (d, 4H), 3.55 (s, 4H), 6.94 (s, 4H), 7.57 (dd, 1H), 7.64 (d, 1H), 7.70 (d, 1H), 7.87 (d, 1H), 7.96 (d, 1H) 10.98 (s, 1H); MS (ES): 555.03 (M+1).

Sodium Salt:

The compound of example 1 (250 mg) was dissolved in excess amount (40-50 mL) of methanol and the reaction mixture was warmed at 60° C. to get a clear solution. To the stirred solution, 1.0 equivalent of sodium hydroxide was added as a solution in methanol. The solution was refluxed for 2-3 hours. After completion of the reaction, the solvent was removed and dried.

mp: 130° C.-133° C.; $^1$H NMR (DMSO-d$_6$): δ 7.88 (d, 1H), 7.60 (d, 1H), 7.46 (d, 1H), 7.43 (d, 1H), 7.40 (dd, 1H), 6.89-6.80 (m, 4H), 3.50 (brs, 4H), 3.04 (t, 2H), 2.97 (t, 2H), 1.97 (s, 3H); MS (ES): 577 [(M−1)+Na].

Example 2

N-(6-(4-(4-Acetylpiperazin-1-yl)phenoxy)-5-chloropyridin-3-yl)-4-methoxybenzene-sulfonamide (Compound 2)

The title compound was obtained by reacting 1-(4-(4-(5-amino-3-chloropyridin-2-yloxy)phenyl)piperazin-1-yl)ethanone (obtained as per procedure described in preparation 2) and 4-methoxybenzene-1-sulfonyl chloride.

$^1$H NMR (DMSO-d$_6$) δ: 1.97 (s, 3H), 3.02 (d, 4H), 3.55 (s, 4H), 3.79 (s, 3H), 6.94 (s, 4H), 7.05-7.08 (m, 2H), 7.63-7.66 (m, 4H), 10.30 (s, 1H); MS (ES): 517.12 (M+1).

Example 3

N-(6-(4-(4-Acetylpiperazin-1-yl)phenoxy)-5-chloropyridin-3-yl)-3,4-dimethoxy-benzene sulfonamide
(Compound 3)

The title compound was obtained by reacting 1-(4-(4-(5-amino-3-chloropyridin-2-yloxy)phenyl)piperazin-1-yl)ethanone (obtained as per procedure described in preparation 2) and 3,4-dimethoxybenzene-1-sulfonyl chloride.

$^1$H NMR (DMSO-d$_6$) δ: 2.06 (s, 3H), 3.02 (d, 4H), 3.55 (s, 4H), 3.74 (d, 6H), 6.94 (s, 4H), 7.05 (d, 1H), 7.19 (s, 1H), 7.25 (d, 1H), 7.64 (s, 2H) 10.26 (s, 1H); MS (ES): 545.16 (M−1).

Example 4

N-(6-(4-(4-Acetylpiperazin-1-yl)phenoxy)-5-chloropyridin-3-yl)-2,5-dimethoxy-benzenesulfonamide
(Compound 4)

The title compound was obtained by reacting 1-(4-(4-(5-amino-3-chloropyridin-2-yloxy)phenyl)piperazin-1-yl)ethanone (obtained as per procedure described in preparation 2) and 2,5-dimethoxybenzene-1-sulfonyl chloride.

$^1$H NMR (DMSO-d$_6$) δ: 2.02 (s, 3H), 3.02 (s, 2H), 3.09 (s, 2H) 3.54 (d, 4H), 3.70 (s, 3H), 3.78 (s, 3H) 6.93 (s, 4H), 7.14-7.20 (m, 3H)) 7.64 (d, 1H) 7.68 (d, 1H), 10.20 (s, 1H); MS (ES): 545.16 (M−1).

Example 5

N-(6-(4-(4-Acetylpiperazin-1-yl)phenoxy)-5-chloropyridin-3-yl)-2-chloro-4-(trifluoromethyl)benzene-sulfonamide (Compound 5)

The title compound was obtained by reacting 1-(4-(4-(5-amino-3-chloropyridin-2-yloxy)phenyl)piperazin-1-yl)ethanone (obtained as per procedure described in preparation 2) and 2-chloro-4-(trifluoromethyl)benzene-1-sulfonyl chloride.

$^1$H NMR (DMSO-d$_6$) δ: 2.01 (s, 3H), 3.02 (d, 4H), 3.54 (s, 4H), 6.93 (s, 4H), 7.69 (s, 2H), 7.8 (d, 1H), 8.13-8.2 (m, 2H), 11.08 (s, 1H); MS (ES): 589.06 (M+1).

Example 6

N-(6-(4-(4-Acetylpiperazin-1-yl)phenoxy)-5-chloropyridin-3-yl)-3,4-dichlorobenzene-sulfonamide (Compound 6)

The title compound was obtained by reacting 1-(4-(4-(5-amino-3-chloropyridin-2-yloxy)phenyl)piperazin-1-yl)ethanone (obtained as per procedure described in preparation 2) and 3,4-dichlorobenzene-1-sulfonyl chloride.

$^1$H NMR (DMSO-d$_6$) δ: 2.02 (s, 3H), 3.03 (s, 2H), 3.1 (s, 2H), 3.55 (s, 4H), 6.92 (s, 4H), 7.62-7.69 (m, 3H)), 7.83 (d, 1H) 7.91 (d, 1H), 10.61 (s, 1H); MS (ES): 554.8 (M−1).

Example 7

N-(6-(4-(4-Acetylpiperazin-1-yl)phenoxy)-5-chloropyridin-3-yl)-4-(trifluoromethoxy)benzenesulfonamide (Compound 7)

The title compound was obtained by reacting 1-(4-(4-(5-amino-3-chloropyridin-2-yloxy)phenyl)piperazin-1-yl)ethanone (obtained as per procedure described in preparation 2) and 4-(trifluoromethoxy)benzene-1-sulfonyl chloride.

$^1$H NMR (DMSO-d$_6$) δ: 2.02 (s, 3H), 3.02 (s, 2H), 3.09 (s, 2H), 3.55 (s, 4H), 6.95 (s, 4H), 7.55 (d, 2H) 7.63-7.67 (m, 2H), 7.83 (d, 2H), 10.58 (s, 1H); MS (ES): 571.03 (M+1).

Example 8

N-(6-(4-(4-Acetylpiperazin-1-yl)phenoxy)-5-chloropyridin-3-yl)-4-methylbenzene-sulfonamide (Compound 8)

The title compound was obtained by reacting 1-(4-(4-(5-amino-3-chloropyridin-2-yloxy)phenyl)piperazin-1-yl)ethanone (obtained as per procedure described in preparation 2) and 4-methylbenzene-1-sulfonyl chloride.

$^1$H NMR (DMSO-d$_6$) δ: 2.02 (s, 3H), 2.33 (s, 3H), 3.02 (s, 2H), 3.09 (s, 2H), 3.55 (s, 4H), 6.94 (s, 4H), 7.34 (d, 2H), 7.58-7.63 (m, 4H)), 10.4 (s, 1H); MS (ES): 501.01 (M+1).)

Example 9

N-(6-(4-(4-Acetylpiperazin-1-yl)phenoxy)-5-chloropyridin-3-yl)-2,4-difluoro benzene-sulfonamide (Compound 9)

The title compound was obtained by reacting the amine 1-(4-(4-(5-amino-3-chloropyridin-2-yloxy)phenyl)piperazin-1-yl)ethanone (obtained as per procedure described in preparation 2) and 2,4-difluorobenzene-1-sulfonyl chloride.

$^1$H NMR (DMSO-d$_6$) δ: 2.02 (s, 3H), 3.01 (t, 2H), 3.08 (t, 2H), 3.55 (s, 4H), 6.95 (s, 4H), 7.22 (t, 1H), 7.51-7.59 (dt, 1H), 7.67 (d, 1H), 7.70 (d, 1H), 7.82-7.9 (m, 1H), 10.86 (s, 1H); MS (ES): 523.09 (M+1).

Example 10

N-(6-(4-(4-Acetylpiperazin-1-yl)phenoxy)-5-chloropyridin-3-yl)-4-fluorobenzene-sulfonamide (Compound 10)

The title compound was obtained by reacting 1-(4-(4-(5-amino-3-chloropyridin-2-yloxy)phenyl)piperazin-1-yl)ethanone (obtained as per procedure described in preparation 2) and 4-fluorobenzene-1-sulfonyl chloride.

$^1$H NMR (DMSO-d$_6$) δ: 2.02 (s, 3H), 3.01 (t, 2H), 3.08 (t, 2H), 3.55 (s, 4H), 6.95 (s, 4H), 7.37 (t, 2H), 7.64 (s, 2H), 7.75-7.80 (m, 2H), 10.48 (s, 1H); MS (ES): 505.1 (M+1).

Example 11

2,4-Dichloro-N-(5-chloro-6-(4-(piperazin-1-yl)phenoxy)pyridin-3-yl)benzene sulfonamide (Compound 11)

The title compound was prepared by deacetylation of N-(6-(4-(4-acetylpiperazin-1-yl)phenoxy)-5-chloropyridin-3-yl)-2,4-dichlorobenzenesulfonamide (obtained as per procedure described in example 1) using concentrated. HCl in methanol-water. N-(6-(4-(4-acetylpiperazin-1-yl)phenoxy)-5-chloropyridin-3-yl)-2,4-dichloro-benzene sulfonamide (500 mg) was dissolved in methanol (100 mL). The mixture was warmed at 50° C. under stirring. To the stirred solution, 2 mL of concentrated HCl and 1 mL of water were added. The resulting solution was stirred for 6-7 hrs at 45-50° C. The solvent was removed and water was added to the residue. The reaction mixture was made alkaline using 1N sodium hydroxide solution. The title compound was precipitated, filtered off and dried under vacuum at 60° C.

Yield: 320 mg (69.3%); $^1$H NMR (DMSO-d6) δ: 3.17 (brs, 4H), 3.19 (brs, 4H), 3.38 (m, 1H), 6.84-6.94 (m, 4H), 7.37 (d, 1H), 7.40-7.45 (m, 2H), 7.58 (d, 1H), 7.91 (d, 1H), 9.95 (s, 1H); MS: 513.1 (M−1).

Example 12

N-(5-Chloro-6-(3-(4-methylpiperazin-1-yl)phenoxy) pyridin-3-yl)-2,4-difluorobenzene sulfonamide (Compound 12)

The title compound was obtained by reacting 5-chloro-6-(3-(4-methylpiperazin-1-yl)phenoxy)pyridin-3-amine (obtained as per procedure described in preparation 3) and 2,4-difluorobenzene-1-sulfonyl chloride.

$^1$H NMR (DMSO-d$_6$) δ: 3.21-3.33 (m, 8H), 3.69 (s, 3H), 6.34 (dd, 1H), 6.46 (d, 1H), 6.50 (d, 1H), 7.06 (t, 1H), 7.25 (dt,

1H), 7.50 (d, 1H), 7.64 (dt, 1H), 7.86 (d, 1H), 7.94 (d, 1H), 10.76 (s, 1H); MS (ES): 493.1 (M−1).

Example 13

N-(5-Chloro-6-(3-(4-methylpiperazin-1-yl)phenoxy)pyridin-3-yl)-4-methoxybenzene-sulfonamide (Compound 13)

The title compound was obtained by reacting 5-chloro-6-(3-(4-methylpiperazin-1-yl)phenoxy)pyridin-3-amine (obtained as per procedure described in preparation 3) and 4-methoxybenzene-1-sulfonyl chloride.

$^1$H NMR (DMSO-$d_6$) δ: 3.22 (t, 4H), 3.33 (s, 4H), 3.69 (s, 3H), 3.78 (s, 3H), 6.34 (dd, 1H), 6.46 (s, 1H), 6.51 (d, 1H), 7.05-7.12 (m, 3H), 7.45 (d, 1H), 7.64 (d, 2H), 7.88 (d, 1H), 10.26 (s, 1H); MS (ES): 489.1 (M+1).

Example 14

4-(6-(4-(4-Acetylpiperazin-1-yl)phenoxy)-5-chloropyridin-3-ylamino)-4-oxobutanoic acid (Compound 14)

The title compound was obtained by reacting 1-(4-(4-(5-amino-3-chloropyridin-2-yloxy)phenyl)piperazin-1-yl)ethanone (obtained as per procedure described in preparation 2) and dihydrofuran-2,5-dione in toluene at reflux temperature. The reaction mixture was concentrated and crude product was purified by column chromatography (silica gel).

$^1$H NMR (DMSO-$d_6$) δ: 2.02 (s, 3H), 2.48 (t, 4H), 3.04 (d, 4H), 3.56 (s, 4H), 6.97 (s, 4H), 8.10 (s, 1H), 8.28 (s, 1H), 10.26 (s, 1H), 12.17 (s, 1H); MS (ES): 447.1 (M+1).

Example 15

N-(6-(2-(Benzo[d]thiazol-2-yl)phenoxy)-5-chloropyridin-3-yl)-2,4-dichlorobenzene-sulfonamide (Compound 15)

The title compound was prepared by reacting 6-(2-(benzo[d]thiazol-2-yl)phenoxy)-5-chloropyridin-3-amine (obtained as per procedure described in preparation 4) and 2,4-dichlorobenzene-1-sulfonyl chloride.

$^1$H NMR (DMSO-$d_6$) δ: 7.26 (d, 1H), 7.39-7.46 (m, 2H), 7.49-7.54 (m, 3H), 7.68 (d, 2H), 7.76 (d, 1H), 7.80 (d, 1H), 7.95-7.98 (m, 2H), 8.06 (d, 1H), 8.39 (dd, 1H); MS (ES): 561.85 (M+1).

Example 16

N-(6-(2-(Benzo[d]thiazol-2-yl)phenoxy)-5-chloropyridin-3-yl)-4-methoxybenzene-sulfonamide (Compound 16)

The title compound was prepared by reacting 6-(2-(benzo[d]thiazol-2-yl)phenoxy)-5-chloropyridin-3-amine (obtained as per procedure described in preparation 4) and 4-methoxybenzene-1-sulfonyl chloride.

$^1$H NMR (DMSO-$d_6$) δ: 3.73 (s, 3H), 6.95 (d, 2H), 7.23 (d, 1H), 7.39-7.45 (m, 2H), 7.49-7.62 (m, 5H), 7.73 (d, 1H), 8.00 (d, 1H), 8.08 (d, 1H), 8.40 (d, 1H); MS (ES): 522.05 (M−1).

Example 17

N-(6-(2-(Benzo[d]thiazol-2-yl)phenoxy)-5-chloropyridin-3-yl)-3,4-dichloro-benzenesulfonamide (Compound 17)

The title compound was prepared by reacting 6-(2-(benzo[d]thiazol-2-yl)phenoxy)-5-chloropyridin-3-amine (obtained as per procedure described in preparation 4) and 3,4-dichlorobenzene-1-sulfonyl chloride.

$^1$H NMR (DMSO-$d_6$) δ: 7.28 (d, 1H), 7.40-7.60 (m, 6H), 7.67 (d, 1H), 7.82 (m, 2H), 7.96 (m, 1H), 8.05 (m, 1H), 8.36 (dd, 1H), 10.65 (s, 1H); MS (ES): 561.90 (M+1).

Example 18

N-(6-(2-(Benzo[d]thiazol-2-yl)phenoxy)-5-chloropyridin-3-yl)-2-chloro-4-(trifluoromethyl)benzene-sulfonamide (Compound 18)

The title compound was prepared by reacting 6-(2-(benzo[d]thiazol-2-yl)phenoxy)-5-chloropyridin-3-amine (obtained as per procedure described in preparation 4) and 2-chloro-4-(trifluoromethyl)benzene-1-sulfonyl chloride.

$^1$H NMR (DMSO-$d_6$) δ: 5.74 (s, 1H), 7.28 (d, 1H), 7.38-7.57 (m, 4H), 7.70 (s, 1H), 7.83 (d, 2H), 7.98 (d, 1H), 8.06 (d, 1H), 8.18 (d, 1H), 8.38 (d, 1H), 11.15 (s, 1H); MS (ES): 593.93 (M−1).

Pharmacology

Example 19

In Vitro Model Exhibiting Insulin Resistance

The assay was designed as in reference, British Journal of Pharmacology, 130, 351-58, 2000, the disclosure of which is incorporated by reference for the teaching of the assay.

The solution of test compound (10 μM/mL) was prepared in DMSO.

Rosiglitazone (0.1 μM in DMSO) was used as standard.

Differentiation into adipocytes was induced by known methods as described below. (J. Biol. Chem., 260, 2646-2652, 1985), the disclosure of which is incorporated by reference for the teaching of adipocyte differentiation.

Culture medium containing 0.5 nM 1-methyl-3-isobutylxanthine (IBMX), 0.25 μM dexamethasone, 5 μg/ml insulin (bovine/human), 10 mM HEPES buffer and fetal bovine serum (FBS) 10% by volume in Dulbecco's modified Eagle's medium (DMEM) was used for differentiation.

3T3 L1 fibroblasts were seeded in 24- or 6-well plates at a density of 0.5-2×10$^4$ cells/well and were allowed to reach maximal confluency.

The confluent fibroblasts were exposed to culture medium for 2 days. After this period, fresh culture medium (DMEM) containing only insulin was used, 10% FBS was added and cultured for 4 days with change of medium every 2 days. After 7 days the cultures received DMEM containing 10% FBS with no exposure to insulin. By the end of 8-10 days, more than 95% of the cells have become differentiated into adipocytes.

The mature adipocytes were exposed to dexamethasone, 100 nM added in ethanol, in culture medium and incubated for 2 days. On the third day, solution of test compound was added along with 100 nM dexamethasone containing medium for 4 days with a change in medium after every 2 days. Vehicle control contained 1% v/v of DMSO. Rosiglitazone was used as a standard and was added at a concentration of 0.1 µM in DMSO, along with 100 nM dexamethasone containing medium for 4 days with a change in medium after every 2 days. After a total period of 6 days, the cells were processed for glucose uptake as follows.

The insulin resistant adipocytes were exposed to serum-free DMEM containing 0.1% bovine serum albumin for 3-4 hours at 37° C. in $CO_2$ atmosphere. The test compound was also present during this period. After 3-4 hours, the medium was aspirated and replaced with Kreb's Ringer phosphate (KRP) buffer at pH 7.4 and with human/porcine insulin, 200 nM. The cells were incubated for 30 minutes at 37° C. At the end of 30 minutes, 0.05 or 0.1 µCi of $^{14}C$-2-deoxyglucose was added to each well of either 24- or 6-well plates respectively and was incubated for exactly 5 minutes. After exactly 5 minutes, the plates were transferred to ice trays and medium was rapidly aspirated. The cell layer was washed twice with ice-cold phosphate buffered saline, (PBS), pH 7.4. Finally the cell layer was lysed with 150 µl of 0.1% sodium dodecyl sulfate (SDS) and the radioactivity of the cell lysate was determined in liquid scintillation counter. Non-specific glucose uptake was assayed in wells exposed to cytochalasin B, inhibitor of glucose transport. Compounds that showed statistically significant increase in the glucose transport/uptake expressed as CPM/well above the level in cells exposed to insulin vehicle are considered actives in this assay. The cut off limit for activity in this IR assay was defined as the increase 1.50 fold of vehicle, assay value of 1.0 for vehicle. Activity was also expressed as % of Rosiglitazone, which is used as a standard for comparison. Statistical analysis was performed using unpaired t-test.

The results are summarized in Table 1.

TABLE 1

Activity of compounds in insulin resistance model

| Sr. No. | Compound No. | Fold Vehicle* | % of Rosiglitazone** |
|---|---|---|---|
| Std | Rosiglitazone | 2.6 ± 0.10 | 100 |
| 01 | 1 | 2.10 ± 0.05 | 61.4 |
| 02 | 4 | 1.55 ± 0.03 | 41.33 |
| 03 | 5 | 1.85 ± 0.04 | 63.94 |
| 04 | 6 | 1.93 ± 0.06 | 69.76 |
| 05 | 14 | 1.49 ± 0.05 | 27.5 |
| 06 | 15 | 2.0 ± 0.13 | 36.7 |

*fold activity over vehicle
**comparison with Rosiglitazone
Conclusion: Representative compounds of the present invention showed insulin sensitizing activity in increasing glucose uptake in the insulin resistance model.

Example 20

(a) Human PPARγ Transactivation Assay

The assay was designed as in the reference, Biochem. Biophys. Res. Comm. 175:865-871, 1991, the disclosure of which is incorporated by reference for the teaching of the assay.

Human PPARγ activity was evaluated by transactivation using a luciferase reporter gene. The pBL-TK-luciferase reporter plasmid AOX-3X PPRE-TK-LUC contains three copies of the rat acyl CoA oxidase PPRE cloned upstream of the minimal herpes simplex virus thymidine kinase (TK) promoter. Human full length PPARγ cDNA was cloned into pSG5 expression vector (Stratagene, Lo Jolla, Calif.).

HEK293 cells were seeded in 24 well plates and grown in DMEM supplemented with 10% (v/v) FCS. After 24 hours, they were transfected with 100 ng of hPPARγ receptor and 300 ng of AOX-3×PPRE-LUC reporter construct per well using Fugen 6 transfection reagent (Roche, Indianapolis, Ind.). Test compounds or Rosiglitazone (dissolved in DMSO) were added 24 hours after transfection. The control was 0.1% DMSO. After 48 hours, transactivation activity was determined by luciferase assay using Steady Glow reagent (Promega, Madison, Wis.). The results are summarized in Table 2.

TABLE 2

Activity of Compound 1 in human PPAR transactivation assay

| Compound No. | PPARγ activity (% of rosiglitazone) |
|---|---|
| Rosiglitazone | 100 |
| 1 | 6.4 |

(b) Mouse PPARγ Assay

The assay was designed as in the reference, Blood, 104(5), 1361-8, 2004, the disclosure of which is incorporated by reference for the teaching of the assay.

3T3-L1 fibroblasts were seeded in 6-well plates at a density of $4 \times 10^4$ cells/well and cultured in DMEM containing 10% calf serum. After 4-5 days, when the cells become confluent, Compound 1 was added (from a 20 mM stock in DMSO) to the final concentration of 50 µM in DMEM supplemented with 10% FCS. Rosiglitazone was added (from 10 mM stock) to a final concentration of 10 µM. The plates were incubated for 72 hrs at 37° C. in a $CO_2$ incubator with fresh medium containing test substances added after first 48 hrs. After 72 hrs, the medium was removed; the cell layer was washed and processed for the PPARγ assay as per the instruction of the manufacturer (Active Motif, North America, California, USA). PPARγ activation was determined using 96-well ELISA assay as per the instruction manual (TransAM PPARγ. Active Motif, Cat 0.40196). Assay Readout was absorbance output from spectrophotometer for the mouse PPARγ assay Luminescence data output was recorded for the human PPARγ assay.

The activity of a compound was expressed as relative activity compared to Rosiglitazone, the reference compound used as positive control. The results are summarized in Table 3.

TABLE 3

Activity of Compound 1 in Mouse PPAR assay

| Compound No. | PPARγ activity (% of rosiglitazone) |
|---|---|
| Rosiglitazone | 100 |
| 1 | 5.1 |

Conclusion: In the selectivity assays for human and mouse PPARγ, the compounds of the present invention did not exhibit any PPARγ activation.

In Vivo Biological Experiments

Note: All animal experimental procedures were approved by Animal Ethics Committee. Compounds which were found active in in vitro assay [Example 19] were subjected to in vivo evaluation in animal models of insulin resistance.

Example 21

Screening in db/db BL/6J Mice

The protocol was designed as in references.
1. Metabolism, 53(12), 1532-1537, 2004.
2. American Journal of Hypertension, 17(5), Supplement 1, S32, 2004.

The disclosures of these two references are incorporated by reference for the teaching of the protocol.

The screening of compounds was based on their ability to reduce the plasma glucose levels in genetically diabetic db/db BL/6J mice.

Male db/db mice (obtained from the Animal House of Nicholas Piramal Research Centre, Goregaon, Mumbai, India) were used for this study (body weight in the range of 30-40 g and age is 6-8 weeks) and were kept eight per cage in individually ventilated cages at controlled temperature (22±1° C.) and humidity (45±5%). Food and water were provided ad libitum during their laboratory stay, except for four hours fasting prior to blood sample collection. 12 hours light and dark cycle was followed during the whole study period.

After 4 hours fasting blood samples were collected from mice. Mice showing plasma glucose levels between 300 to 500 mg/dl were divided in groups (8-10 per group) such that the mean plasma glucose levels and variation within the group, for each group, is nearly the same. After grouping, mice in respective groups received treatment with 0.5% CMC vehicle, standard compound or test compounds for 10 days. Rosiglitazone was used as a standard.

After 4 hours fasting, mice were anaesthetized using isoflurane (inhalation anesthetic), and blood samples were collected through the retro orbital plexus. Collected blood samples were centrifuged at 7000 rpm for 10 minutes at 4° C.; Separated plasma was used for estimation of plasma glucose using diagnostic kits (Diasys, Germany). Plasma glucose levels of treated groups were normalized with control group using the following formula, which accounted for the changes in control group.

Formula used for normalization was

*: {1−(Ratio of mean plasma glucose levels of control group on day 10 to day 0)/(Ratio of plasma glucose levels of treated group on day 10 to day 0)}×100.

The results are summarized in Table 4.

TABLE 4

Reduction in the plasma glucose levels in genetically diabetic db/db BL/6J mice.

| Sr. No | Compounds tested in db/db mice | | | Rosiglitazone tested in db/db mice | |
|---|---|---|---|---|---|
| | Compound No. | Dose (10 days) | Normalization with control* | Dose (10 days) | Normalization with control* |
| 01 | 1 | 100 mpk bid | 46.07 ± 4.55 | 5 mpk bid | 55.73 ± 4.46 |
| 02 | 14 | 100 mpk bid | Inactive | 5 mpk bid | 53.34 ± 4.11 |

Formula used for normalization:
*{1 − (Ratio of mean plasma glucose levels of control group on day 10 to day 0)/(Ratio of plasma glucose levels of treated group on day 10 to day 0)} × 100
Conclusion: A representative Compound of the present invention showed significant glucose lowering activity in the animal model of diabetes.

Example 22

Evaluation of Antiobesity

The assay was designed as in reference, PCT publication WO 2003086306, the disclosure of which is incorporated by reference for the teaching of the assay.

(a) Acute Study

Male C57Bl6/J mice, weighing 20-25 g, were housed individually in the animal facility. Water and Chow (Amrut Laboratory Animal feed, Sangli, Maharashtra, India) were available ad libitum. One day before the study, the animals were weighed and separated into treatment groups having similar average body weight. For the experiment, the animals were deprived of food overnight for 16 hours. They were dosed intraperitoneally with test compounds (100 mg/kg) or comparator standard (Sibutramine, 3 mg/kg) in saline vehicle (10 mL/kg). Half an hour after drug administration the animals were presented with a pre-weighed amount of food in the food cup. Food that remained in the cup was measured at various time points. The effect of standard, and test compounds on food intake in fasted lean C57Bl6/J mice at 2, 4, 6 and 24 hrs post-food introductions was evaluated. The results are as indicated in FIG. 1.

Conclusion: Compound 1 and Compound 11 are effective in inhibiting food intake of C57Bl6/J mice for 2 hours after food introduction. (*** $p<0.001$ vs vehicle treated controls)

(b) Chronic Study

Figure 2:
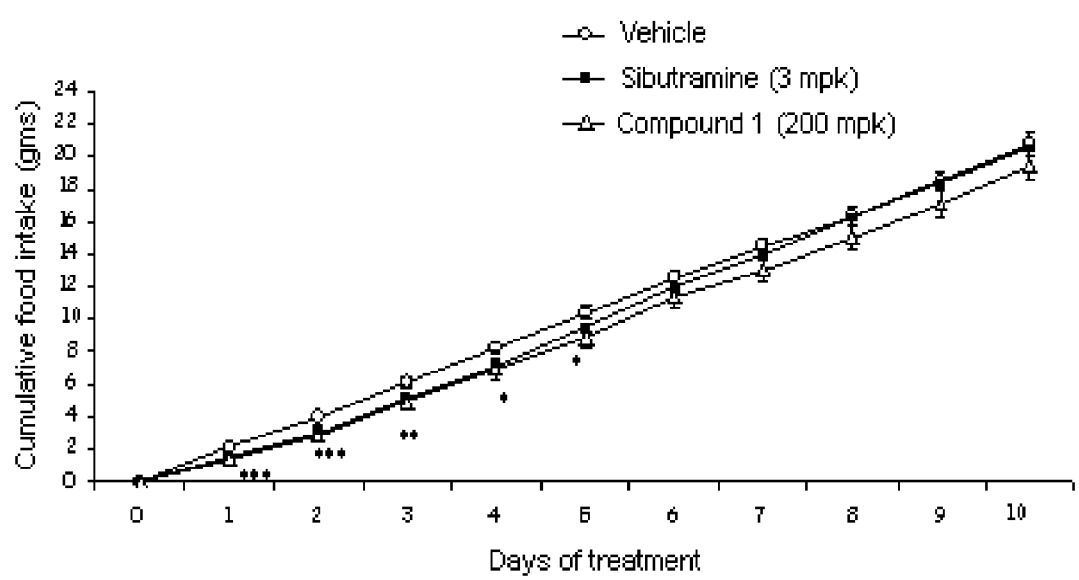
FIG. 2: Effect of Compound 1 on cumulative food intake of diet induced obese mice.
Diet induced obese (DIO) mice were treated with either standard (Sibutramine) or Compound 1 for 10 days.
Figure 3:
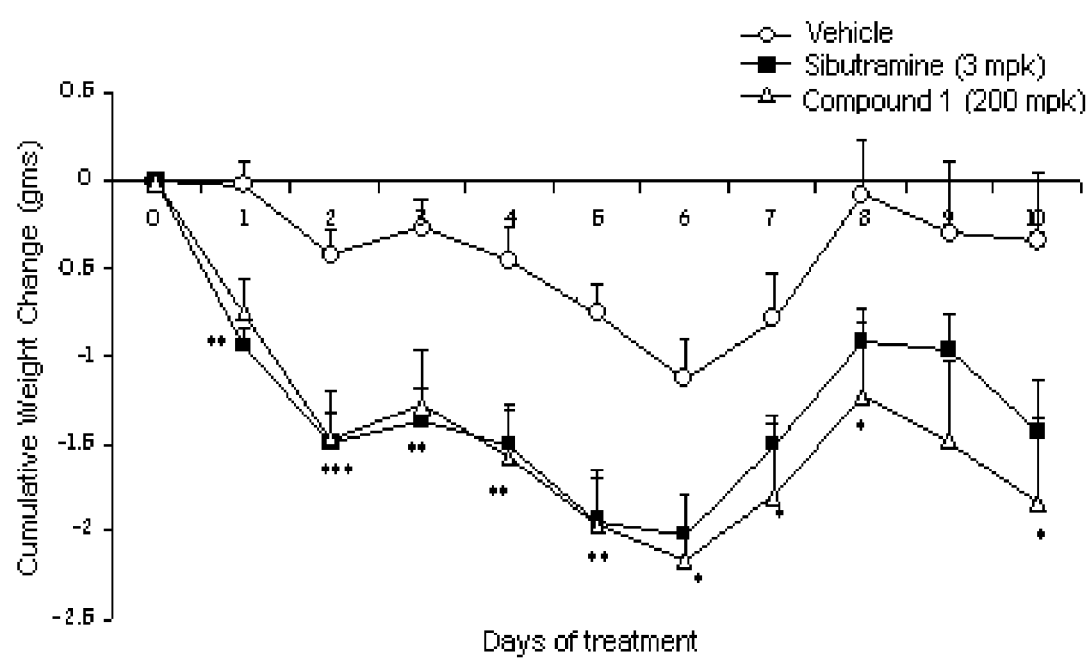
FIG. 3: Effect of Compound 1 on body weight in diet induced obese mice.
Cumulative body weight gain of diet induced obese (DIO) mice treated with either standard (Sibutramine) or Compound 1 for 10 days is indicated.

The assay was designed as in the reference, British Journal of Pharmacology, 132, 1898-1904, 2001, the disclosure of which is incorporated by reference for the teaching of the assay. Male C57Bl6/J mice (3-4 weeks of age) were housed in groups of 10 animals per cage in the animal facility. High fat diet (D12451 Research Diets Inc., New Brunswick, N.J. 08901, USA), 45% kcal from fat) and water were provided ad libitum for 14 weeks. After this period, the animals were housed individually in cages. The animals were weighed and separated into groups with similar body weight. They were acclimatized to the experimental procedures for 2 days Animals were dosed intraperitoneally with test compound (200 mg/kg) or the standard (Sibutramine, 3 mg/kg) in 10 ml/kg of 0.5% CMC vehicle between 10:00 h-12:00 h. After drug administration the animals were presented with a pre-weighed amount of food in the food cup. Weight of feed remaining in the cup and body weight were recorded daily just prior to dosing. The change in weight and cumulative food intake were computed. The results are indicated in FIG. 2 and FIG. 3.

Conclusions: 1. Compound 1 was effective in reducing cumulative food intake of diet induced obese (DIO) mice during the 10 days of treatment. (* $p<0.001$,  $p<0.01$, * $p<0.05$ vs vehicle treated controls).

2. Compound 1 was effective in reducing cumulative body weight gain of diet induced obese (DIO) mice during the 10 days of treatment. (* $p<0.001$,  $p<0.01$, * $p<0.05$ vs vehicle treated controls).

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

The invention claimed is:

1. A method for the treatment of a metabolic disorder related to insulin resistance or hyperglycemia, comprising:
    administering to a mammal in need thereof a therapeutically effective amount of a compound of formula (I), or a stereoisomer or pharmaceutically acceptable salt thereof, the formula (I) is represented by:

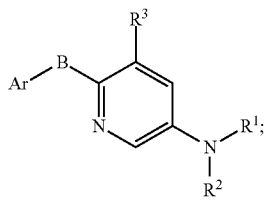

Formula (I)

wherein:
    Ar is a phenyl group substituted with heterocyclyl or heteroaryl, wherein the heterocyclyl or heteroaryl group may be unsubstituted or substituted;
    B is —O—, —S—, or —NH—;
    $R^1$ is hydrogen;
    $R^2$ is $S(O)_2R^4$ or $C(O)(CH_2)_n$—$C(O)OR^5$;
    $R^3$ is halogen, cyano, $(CO)OR^6$, or $C(O)NR^7R^8$;
    $R^4$ is unsubstituted or substituted aryl;
    $R^5$ is hydrogen, $(C_1-C_6)$alkyl, or unsubstituted or substituted aryl;
    $R^6$ is hydrogen or $(C_1-C_4)$alkyl;
    $R^7$ and $R^8$ are independently hydrogen or $(C_1-C_6)$alkyl; and
    n is an integer from 1-3;
wherein the metabolic disorder related to inulin resistance or hyperglycemia is selected from type 2 diabetes, obesity, glucose intolerance, dyslipidemia and hyperinsulinemia.

2. The method according to claim 1;
wherein, in the compound of formula (I):
    Ar is a phenyl group substituted with heterocyclyl, wherein the heterocyclyl group may be unsubstituted or substituted;
    B is —O—;
    $R^1$ is hydrogen;
    $R^2$ is $S(O)_2R^4$;
    $R^3$ is halogen; and
    $R^4$ is unsubstituted or substituted aryl.

3. The method according to claim 2;
wherein, in the compound of formula (I):
    Ar is a phenyl group substituted with piperazinyl with the phenyl moiety coupled to B, wherein the piperazinyl group may be unsubstituted or substituted;
    B is —O—;
    $R^1$ is hydrogen;
    $R^2$ is $S(O)_2R^4$;
    $R^3$ is chlorine; and
    $R^4$ is 4-methylphenyl, 2-chloro-4-trifluoromethylphenyl, 3,4-dimethoxyphenyl, 2,5-dimethoxyphenyl, 4-methoxyphenyl, 4-trifluoromethoxyphenyl, 4-fluorophenyl, 2,4-difluorophenyl, 2,4-dichlorophenyl, or 3,4-dichlorophenyl.

4. The method according to claim 3;
wherein, in the compound of formula (I):
    Ar is 4-(4-acetyl-piperazin-1-yl)phenyl with the phenyl moiety coupled to B;
    B is —O—;
    $R^1$ is hydrogen;
    $R^2$ is $S(O)_2R^4$;
    $R^3$ is chlorine; and
    $R^4$ is 4-methylphenyl, 3,4-dimethoxyphenyl, 2,5-dimethoxyphenyl, 4-methoxyphenyl, 4-trifluoromethoxyphenyl, 4-fluorophenyl, 2,4-difluorophenyl, 2,4-dichlorophenyl, 3,4-dichlorophenyl, or 2-chloro-4-trifluoromethylphenyl.

5. The method according to claim 1;
wherein, in the compound of formula (I):
    Ar is a phenyl group substituted with heteroaryl, wherein the heteroaryl group may be unsubstituted or substituted;
    B is —O—;
    $R^1$ is hydrogen;
    $R^2$ is $S(O)_2R^4$;
    $R^3$ is chlorine; and
    $R^4$ is unsubstituted or substituted aryl.

6. The method according to claim 5;
wherein in the compound of formula (I):
    Ar is 6-(2-benzo[d]thiazol-2-yl)phenyl with the phenyl moiety coupled to B;
    B is —O—;
    $R^1$ is hydrogen;
    $R^2$ is $S(O)_2R^4$;
    $R^3$ is chlorine; and
    $R^4$ is 4-methoxyphenyl, 2,4-dichlorophenyl, 3,4-dichlorophenyl, or 2-chloro-4-trifluoromethylphenyl.

7. The method, according to claim 1;
wherein, in the compound of formula (I):
    Ar is a phenyl group substituted with heterocyclyl with the phenyl moiety coupled to B; wherein the heterocyclyl group may be unsubstituted or substituted;
    B is —O—;
    $R^1$ is hydrogen;
    $R^2$ is $C(O)(CH_2)_n$—$C(O)OR^5$;
    $R^3$ represents halogen, cyano, $(CO)OR^6$, or $C(O)NR^7R^8$;
    $R^5$ is hydrogen, $(C_1-C_6)$alkyl, or unsubstituted or substituted aryl;
    $R^6$ is hydrogen or $(C_1-C_4)$alkyl;
    $R^7$ and $R^8$ are independently hydrogen or $(C_1-C_6)$alkyl; and
    n is an integer from 1-3.

8. The method, according to claim 1;
wherein the compound of formula (I) is selected from:
    N-(6-(4-(4-Acetylpiperazin-1-yl)phenoxy)-5-chloropyridin-3-yl)-2,4-dichlorobenzene-sulfonamide,
    N-(6-(4-(4-Acetylpiperazin-1-yl)phenoxy)-5-chloropyridin-3-yl)-4-methoxybenzene-sulfonamide,
    N-(6-(4-(4-Acetylpiperazin-1-yl)phenoxy)-5-chloropyridin-3-yl)-3,4-dimethoxy-benzene sulfonamide,
    N-(6-(4-(4-Acetylpiperazin-1-yl)phenoxy)-5-chloropyridin-3-yl)-2,5-dimethoxy-benzene sulfonamide,
    N-(6-(4-(4-Acetylpiperazin-1-yl)phenoxy)-5-chloropyridin-3-yl)-2-chloro-4-(trifluoromethyl)benzene-sulfonamide, N-(6-(4-(4-Acetylpiperazin-1-yl)phenoxy)-5-chloro-pyridin-3-yl)-3,4-dichlorobenzene-sulfonamide,
N-(6-(4-(4-Acetylpiperazin-1-yl)phenoxy)-5-chloro-pyridin-3-yl)-4-(trifluoromethoxy)benzene-sulfonamide,
N-(6-(4-(4-Acetylpiperazin-1-yl)phenoxy)-5-chloro-pyridin-3-yl)-4-methylbenzene-sulfonamide,
N-(6-(4-(4-Acetylpiperazin-1-yl)phenoxy)-5-chloro-pyridin-3-yl)-2,4-difluorobenzene-sulfonamide,
N-(6-(4-(4-Acetylpiperazin-1-yl)phenoxy)-5-chloro-pyridin-3-yl)-4-fluorobenzene-sulfonamide,
2,4-Dichloro-N-(5-chloro-6-(4-(piperazin-1-yl)phenoxy)pyridin-3-yl)benzenesulfonamide,
N-(5-Chloro-6-(3-(4-methylpiperazin-1-yl)phenoxy)pyridin-3-yl)-2,4-difluorobenzene sulfonamide,
N-(5-Chloro-6-(3-(4-methylpiperazin-1-yl)phenoxy)pyridin-3-yl)-4-methoxybenzene-sulfonamide,
4-(6-(4-(4-Acetylpiperazin-1-yl)phenoxy)-5-chloropyridin-3-ylamino)-4-oxobutanoic acid,
N-(6-(2-(Benzo[d]thiazol-2-yl)phenoxy)-5-chloropyridin-3-yl)-2,4-dichlorobenzene-sulfonamide,
N-(6-(2-(Benzo[d]thiazol-2-yl)phenoxy)-5-chloropyridin-3-yl)-4-methoxybenzene-sulfonamide,
N-(6-(2-(Benzo[d]thiazol-2-yl)phenoxy)-5-chloropyridin-3-yl)-3,4-dichloro-benzenesulfonamide, and
N-(6-(2-(Benzo[d]thiazol-2-yl)phenoxy)-5-chloropyridin-3-yl)-2-chloro-4-(trifluoromethyl)benzene-sulfonamide.

9. The method according to claim 1;
wherein the metabolic disorder related to insulin resistance or hyperglycemia is type 2 diabetes.

10. The method according to claim 1;
wherein the metabolic disorder related to insulin resistance or hyperglycemia is obesity.

* * * * *